(12) United States Patent
Fujimaki et al.

(10) Patent No.: US 7,792,575 B2
(45) Date of Patent: Sep. 7, 2010

(54) LANGUAGE PROCESSING FUNCTION MEASURING DEVICE

(75) Inventors: Norio Fujimaki, Koganei (JP); Tomoe Hayakawa, Koganei (JP); Hitoshi Isahara, Koganei (JP); Kyouko Kanzaki, Koganei (JP)

(73) Assignee: National Institute of Information and Communications Technology, Tokyo (JP)

( * ) Notice: Subject to any disclaimer, the term of this patent is extended or adjusted under 35 U.S.C. 154(b) by 1248 days.

(21) Appl. No.: 11/349,810

(22) Filed: Feb. 8, 2006

(65) Prior Publication Data
US 2006/0178597 A1 Aug. 10, 2006

(30) Foreign Application Priority Data
Feb. 10, 2005 (JP) .......................... P2005-035129

(51) Int. Cl.
*A61B 5/00* (2006.01)
(52) U.S. Cl. ........................................ 600/544; 600/300
(58) Field of Classification Search ........................ None
See application file for complete search history.

(56) References Cited

U.S. PATENT DOCUMENTS

| | | | |
|---|---|---|---|
| 2002/0062089 A1* | 5/2002 | Johnson, Jr. | 600/544 |
| 2005/0065413 A1* | 3/2005 | Cacioppo et al. | 600/300 |
| 2007/0049844 A1* | 3/2007 | Rosenfeld | 600/544 |

FOREIGN PATENT DOCUMENTS

JP 2001-037733 2/2001

OTHER PUBLICATIONS

Henson, R.N.A. "Neuroimaging Studies of Priming"; Progress in Neurobiology, London, UK; May 19, 2003; pp. 54-81.
Ihara, Aya et al. "Lexical Access and Selection of Contextually Appropriate Meaning for Ambiguous Words"; NeuroImage, Science Direct; Jul. 19, 2007; pp. 576-588.
Wei, Qiang et al. "Phonological Influences on Lexicosemantic Processing of Kanji Words"; NeuroReport—Cognitive Neuroscience and Neuropsychology; Kobe, Hyogo, Japan, Aug. 17, 2007; pp. 1775-1780.
Fujimaki, Norio et al. "Masked Immediate-Repetition-Priming Effect on the Early Lexical Process in the Bilateral Anterior Temporal Areas Assessed by Neuromagnetic Responses"; (Manuscript) pp. 1-39.

* cited by examiner

*Primary Examiner*—Robert L Nasser

(57) ABSTRACT

The device of the present invention can automatically extract words under accurately controlled set conditions. A word presenting means presents words to a subject, a biological activity measuring means measures the biological activity in the subject, and a calculation means receives a biological activity signal from the biological activity measuring means and calculates time from presenting the words until detecting a biological activity by the subject accompanied with the word. The calculation means is equipped with a word database where word data indicating words are stored and can be presented to the subject, a category data of the words and attribute data of the words are related and also stored, respectively, and a word extractor to search the word database and to extract the word data belonging to or relating to a predetermined category, and, satisfying predetermined word attribute, based upon the search conditions. The word presenting means presents a portion of or entire words indicated by the word data extracted by the word presenting means to the subject.

15 Claims, 6 Drawing Sheets

WORD FAMILIARITY

| READING | NOTATION | CHARACTER&SOUND | SOUND | CHARACTER |
|---|---|---|---|---|
| …… | …… | …… | …… | …… |
| RINKO | RINKO(KANJI) | 2.125 | 1.719 | 2.000 |
| RINGO | RINGO(KANJI) | 6.500 | 6.500 | 6.719 |
| RINKOU | RINKOU(KANJI) | 2.312 | 2.844 | 2.406 |
| …… | …… | …… | …… | …… |

FIG.4

| NOTATION PROPRIETY | |
|---|---|
| NOTATION | PROPRIETY |
| ...... | ...... |
| RINKO(HIRAGANA) | 2.55 |
| RINKO(KATAKANA) | 1.40 |
| RINKO(KANJI) | 4.50 |
| RINGO(HIRAGANA) | 4.15 |
| RINGO(KATAKANA) | 4.05 |
| RINGO(KANJI) | 4.30 |
| RINKO(KANJI) | 2.35 |
| ......... | ......... |

FIG.5

LANGUAGE PROCESSING FUNCTION MEASURING DEVICE

BACKGROUND OF THE INVENTION

1. Field of the Invention

The present invention relates to a language processing function measuring device for conducting experiments relating to language processing of subjects, and more particularly for automatically selecting words for presentation to a subject under preset conditions while minimizing errors in the measured data.

2. Description of Related Art

A language experiment (for example Japanese Patent Laid-Open Publication No. 2001-37733), such as a priming experiment where a first word (prime), which is regarded to as precedent stimulant, is presented to a subject, and after a certain period of time has passed, a second word (target), which is regarded to as subsequent stimulant, is presented, and the reaction time to the second word is measured, is conventionally conducted.

In this language experiment, it is necessary to prepare a list of words to be presented to the subject in advance, and conventionally, in the preparation of this list of words, words whose category and lexical properties match desired conditions are extracted mainly from materials, such as newspapers, magazines, books or dictionaries, by hand.

However, it takes time and efforts for this extraction task because full determination has to be made to each word from gigantic materials; in addition, inappropriate words have to be excluded according experience and propriety has to be confirmed with respect to a subject group, which is correspondent to target age, sex and educational background, using a questionnaire(s).

Further, since this extraction task is conducted by hand, even though words satisfy set conditions, the degree of satisfying the conditions is different per word, and as a result, it will adversely affect measurement data, and then, a defect not to be able to obtain reliable experimental results will also occur.

In addition, more than a certain number of words are required for the experiment. However, because there is a so-called trade-off relationship between the number of words to be extracted and the number and/or severity of set conditions, if the extraction task is conducted by hand, it is very difficult to find appropriate conditions for a short time and to obtain the desired number of words, and there is also a problem that it takes a long time for trial and error regarding which condition can be relaxed for the purpose of obtaining the desired number of words or how to set the conditions.

SUMMARY OF THE INVENTION

The present invention has been accomplished to solve the above problems, and a desired object is to extract words, which are accurately controlled by a set of predetermined conditions.

In other words, the language processing function measuring device relating to the present invention is a language processing function measuring device equipped with a word presenting unit to present words to subjects; a biological activity measuring unit to measure the biological activity in the subjects; and a calculation unit to receive a biological activity signal from the biological activity measuring unit and to calculate the period of time from presenting the words to initiating the biological activity accompanied with the words by the subjects, or the information regarding the biological activity position;

The calculation unit is equipped with a word database for recording word data indicating words to be presented to the subjects, category data of the words and attribute data of the words are related and then stored, respectively, and a word extractor to search the word database and to extract the word data belonging to or relating to a predetermined category, and satisfying a predetermined word attribute, based upon search conditions, and, the word presenting unit presents a portion of or entire words indicated by the word data extracted by the word extractor.

With this device, because words accurately controlled by set conditions can be extracted, time and efforts required for the word extraction can be reduced. In addition, an effect on measurement data due to inappropriateness of controlled conditions can be as little as possible, and the reliability of experimental results can be improved. Further, the condition setting to be able to obtain the required number of words can be fed back, and the desired number of words can be obtained without trial and error by manual procedures.

Further, the differentiation of the number of words to be presented may cause a movement while the subject is glancing at the presented word, and this can result in an effect on the reaction, such as brain activity. In order to resolve this defect, it is additionally desirable that the word extractor extracts word data indicating words with a predetermined number of characters.

As a specific embodiment, it can be considered that the category hierarchically indicates the classification of words, and the attribute contains word familiarity, which is an index indicating how likely the word is to be familiar to the subject, and representational plausibility, which is an index indicating the plausibility of word representation, such as Katakana, Hiragana or Kanji character. This is an example of different symbols used to represent the Japanese language. If there are multiple notations of representing words in other languages, than similar indices can also be used for those languages. Further, the predetermined attribute can be a concept including a visual form, phonology and semantics, as well.

For example, in order to use a priming experiment, it is desirable that the word presenting unit presents at least the first word and the second word, which are established from the word data extracted by the word extractor, at a predetermined time interval to subjects, respectively.

As a specific embodiment, it can be considered that the biological activity measuring unit is equipped with a brain activity measuring unit to measure a brain activity in the subjects, and the calculation unit is equipped with a brain activity data calculator to calculate at least either the brain activity time period indicating the time variation of the brain activity in the subjects or the brain activity position data indicating the position of the brain activity in the subjects, based upon the brain activity measurement data from the brain activity measuring unit.

Similarly, it can be considered that the biological activity measuring unit is equipped with an operation unit to be subjectively operated when the subjects recognize said word and decide an answer to the question on the words that are asked prior to the experiment, and the calculation unit is equipped with an action index calculator to calculate action index data indicating at least either the reaction time or the percentage of questions answered correctly by the subjects, based upon an operation signal from the operation unit.

In order to be able to variously set conditions in response to objectives of the language processing function measurement, it is desirable that the present invention be equipped with a search condition acceptor for accepting search conditions from an operator, and the word extractor searches from word database and extracts word data for indicating words belonging to or relating to a predetermined category, and, satisfying the desired word attribute, based upon the search conditions set by the operator in addition, extracts the word data indicating words with the predetermined number of characters, based upon the search conditions set by the operator.

As a specific embodiment to enter search conditions, it can be considered that the search conditions are composed of multiple logical formulae for the search conditions. Herein, the "logical formulae" contain logical SUM, logical AND, logical INVERT and combination of these operatives.

As described above, according to the present invention, words, which are accurately controlled by the set condition, can be extracted, so time and efforts required for the word extraction can be reduced. In addition, a variable effect on the measurement data can be reduced, and the reliability of experimental results can be improved. Then, the condition setting where the necessary number of words can be obtained can be fed back, and the desired number of words can be obtained in a short period of time.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 4 is a table showing the word familiarity in said embodiment;

FIG. 5 is a table showing the representational plausibility in said embodiment.

DETAILED DESCRIPTION OF THE PREFERRED EMBODIMENTS

Figure 1:
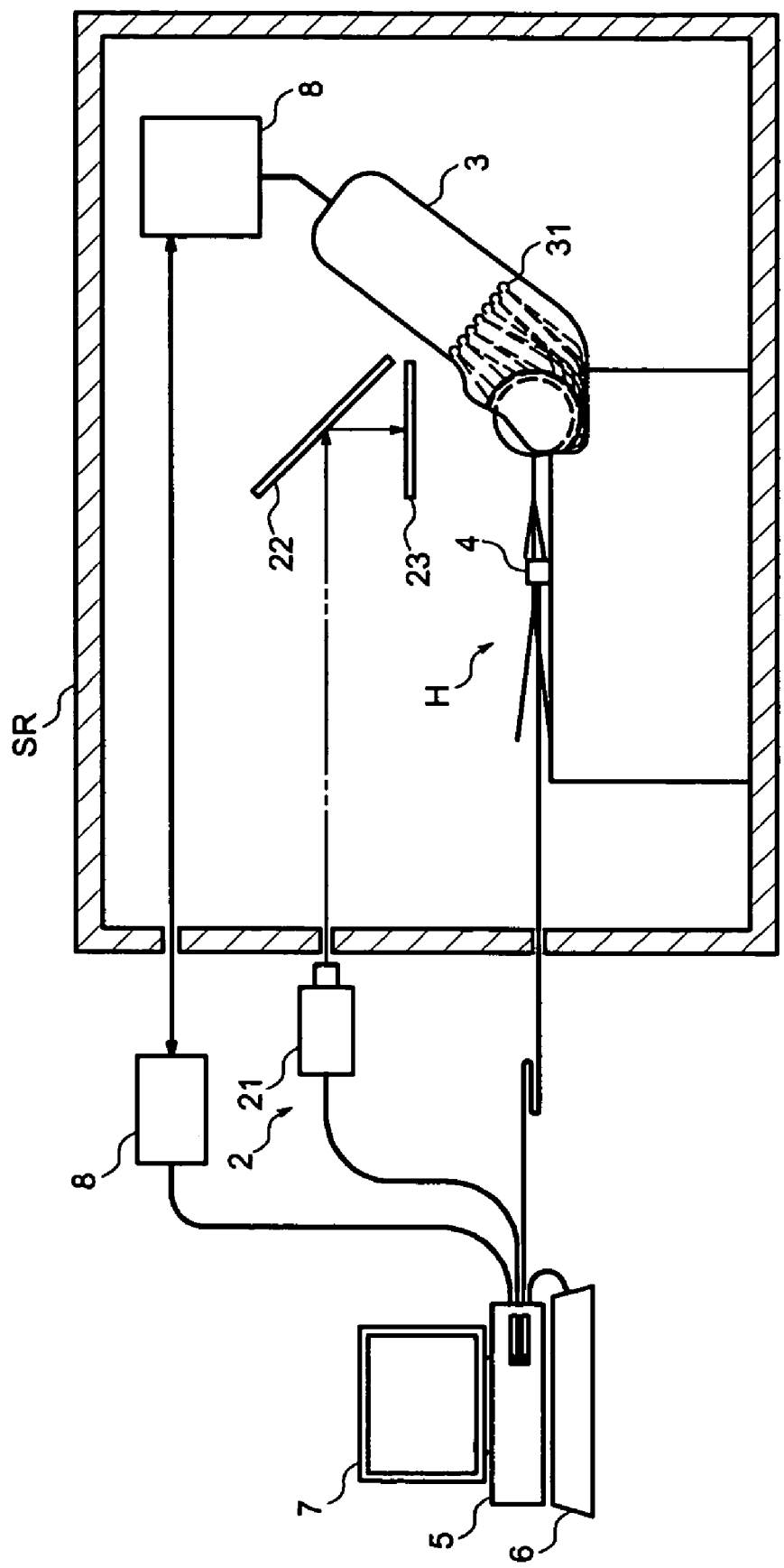
FIG. 1 is a typical block diagram of a language processing function measuring device relating to the present embodiment.

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Hereafter, an embodiment of the present invention is described with reference to the drawings. In the drawings the term means has been utilized to refer to a unit or device and can include software that enables a computer or controller to perform various tasks such as process signals for measuring brain activity, search for words and calculate brain activity and the position of brain activity. Likewise, hardware and logic circuits can be provided to perform such tasks.

A language processing function measuring device 1, as typically shown in FIG. 1, is equipped with a word presenting means or unit 2 to present words to a subject H, a brain activity measuring means or unit 3 to measure a predetermined brain activity in the subject H, an operation means or unit 4 to be subjectively operated when the subject H recognizes the words, and a calculation device 5.

The word presenting unit 2 is composed of a projection means or unit 21 to project a word extracted by a word extractor 52 as an image, a mirror 22 for reflecting the image from the projection unit 21 to the subject H, and a translucent screen 23 where the subject H actually sees the projected word. Furthermore, within the range not to affect a brain activity measurement, a word indicated by the word data transmitted from the calculation device 5 can be displayed on the screen using, for example, a CRT display, a liquid crystal display or a plasma display.

The projection unit 21, for example, is a projector, and it presents a first word (prime) between a pair of the words acquired by a below-described word acquirer 53 for approximately 0.1 second, and then, after a certain period of time (for example, 0.5 to 1 second) has passed, it presents a second word (target) for approximately 0.1 second. After that, a new pair of words, the first word (prime) and the second word (target), are similarly presented to the subject H at 2 to 3 seconds of interval. Depending upon experiments, after the second word is presented, third, fourth . . . words can be presented.

The brain activity measuring unit 3 is a brain magnetically field measuring device (Magnetoencephalography: MEG) using a SQUID magnetic sensor 31, and it is installed within the magnetically shielded room SR.

The operation unit 4 is a push button, a joystick or a keyboard operated by the subject H when the subject H recognizes the words displayed on the translucent screen 23 by the word displaying means 2, and it is constructed such that when the subject H operates the operation means 4, an operation signal is transmitted to the calculation device 5.

Figure 2:
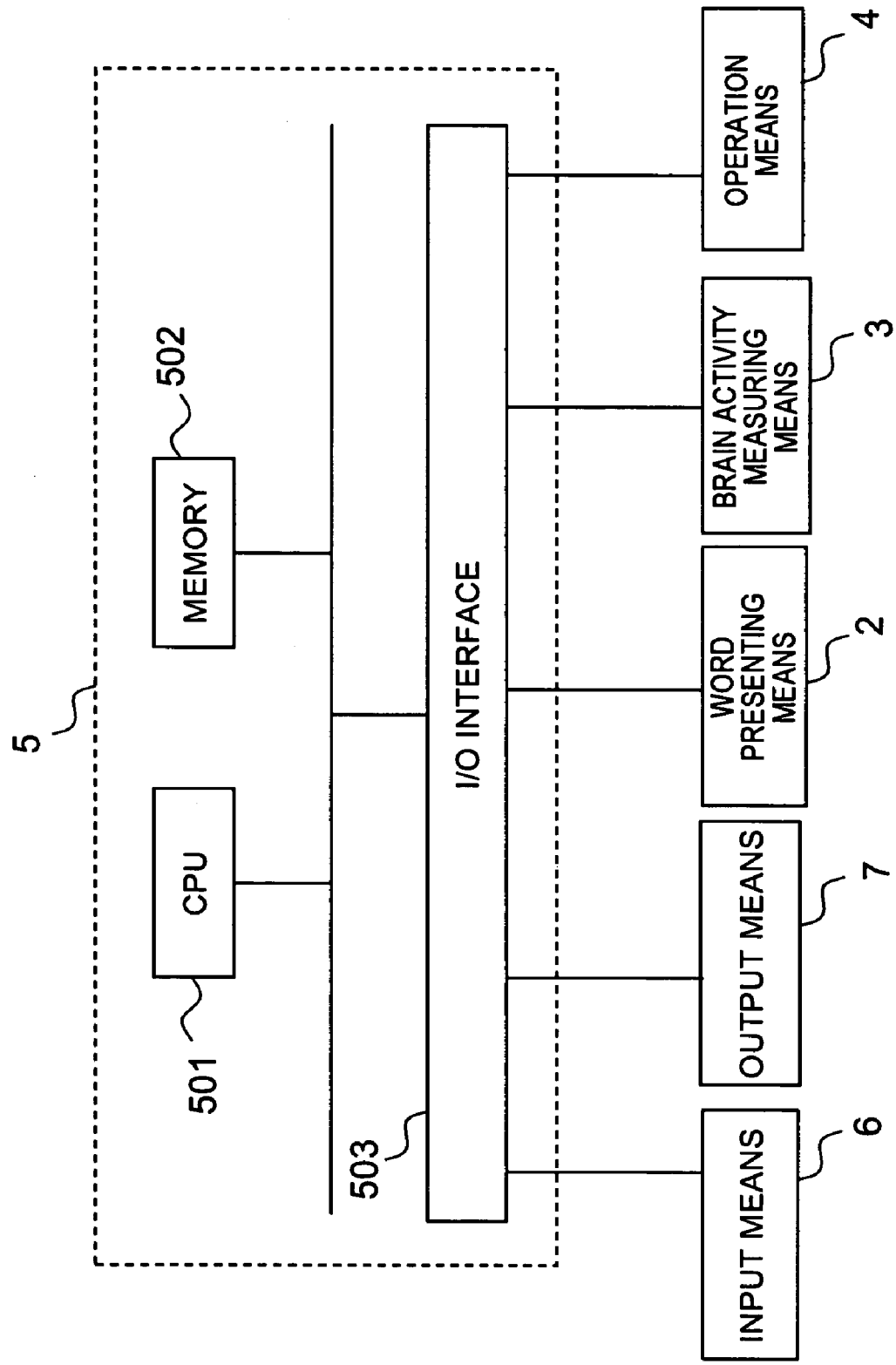
FIG. 2 is an instrument block diagram of a calculation device in said embodiment.
Figure 3:
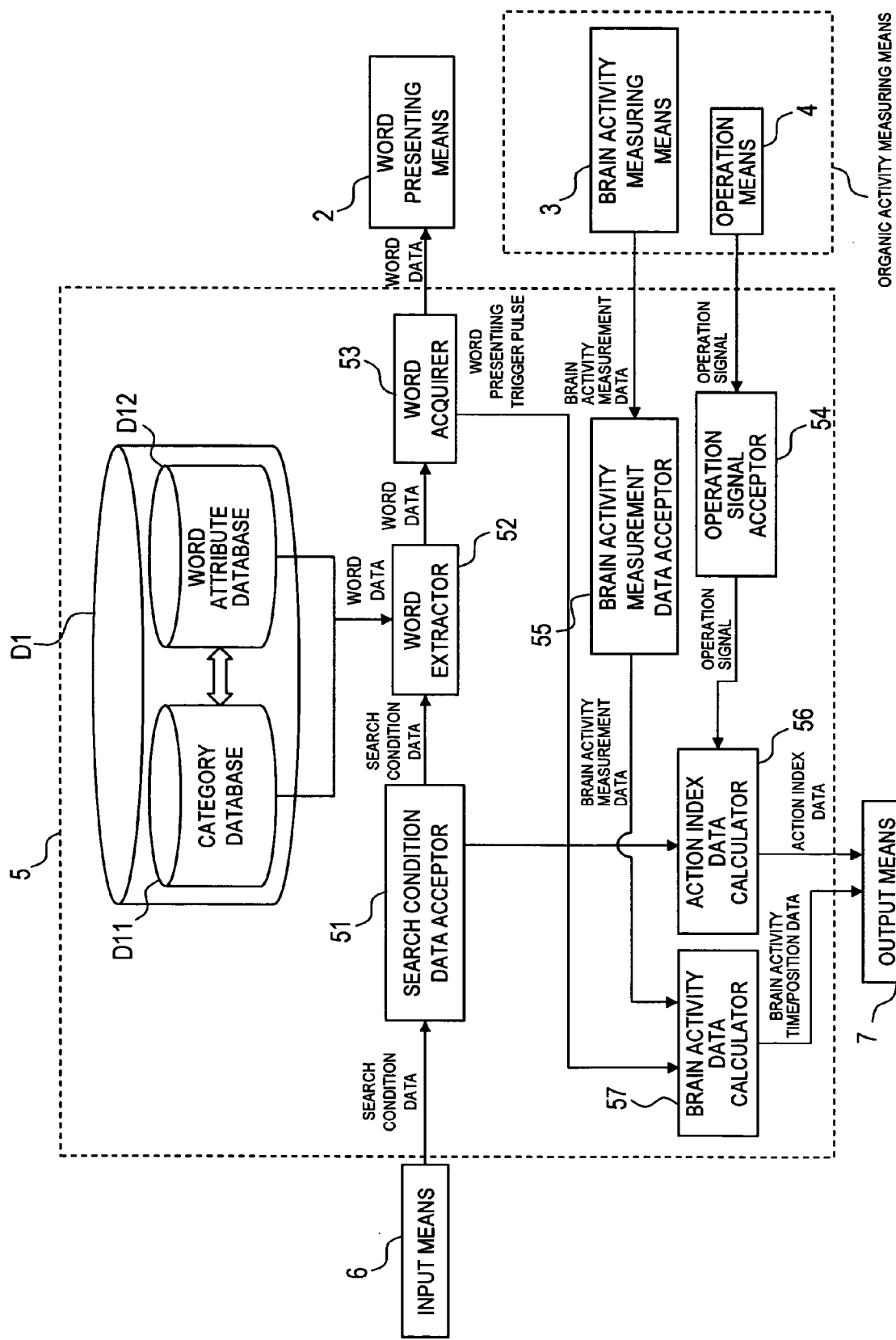
FIG. 3 is a functional block diagram of the calculation device in said embodiment.

The calculation device 5, as shown in FIG. 2, can be a so-called computer equipped with a CPU 501, a nonvolatile or volatile memory 502 and an I/O interface 503, and an input means 6, such as a keyboard or a mouse, and an output means 7, such as a display, are connected, and cooperation with each peripheral device including the CPU 501 in accordance with a predetermined program stored in the memory 502, as shown in FIG. 3, results in the demonstration of functions as a word database D1, a search condition data acceptor 51, a word extractor 52, the word acquirer 53, an operation signal acceptor 54, a brain activity measurement data acceptor 55, an action index data calculator 56 and a brain activity data calculator 57. The related calculation device 5 can also function where each of the D1 and 51 to 57 by a single unit, and it can be functioned as each of the components D1 and 51 to 57 are processed separately by multiple computers. It is needless to say, it can be constructed by programming software in the memory utilizing a general-purpose computer, and it can be totally or partially constructed with hardware using an exclusive use logic circuit.

Hereafter, each portion is described in detail.

The word database D1 is composed of a category database D11 where words are classified per category and a word attribute database D12 where values indicating an attribute are stored per word. The word familiarity data, which is a digitized index indicating how much the word is familiar to a person in the subject population, and the representational plausibility data, which is a digitized index indicating the plausibility of word representation, such as Katakana, Hiragana and Kanji, are stored per word within the word attribute database D12. Specifically, they are stored with the formats shown in FIG. 4 and FIG. 5, respectively.

The search condition data acceptor 51 receives the search condition data entered by the operator using the input means 6 and the logical data among the search conditions, and transmits them to the word extractor 52. Herein, the logic formulae can indicate logical SUM, logical AND, logical INVERT and any combination of these.

The word extractor 52 searches the category database D11 and the word attribute database D12 stored in the word database D1 in a cross-sectoral manner, based upon the search condition data and the logical formula data, and extracts the word data indicating words satisfying the category and the attribute to be determined by the search conditions.

As possible search conditions, there can be a condition belonging to each category required from an experimental theme, such as "food," "sports" and "animals"; a condition for the number of characters; a condition for each character representation of Katakana/Hiragana/and combination of Kanji and Hiragana; a condition for the word familiarity; and a condition for the representational plausibility.

As specific search conditions, when individual conditions, such as "food" for the category, three for the number of characters, Katakana for the representation, 6 or greater in 7 ranks for the word familiarity, and 4 or greater in 5 ranks for the representational plausibility, are entered, in addition, if the logical AND of these individual conditions is regarded as the search condition, the word extractor 52 extracts the word data indicating the data where the category indicates "food" from the category database first; determines whether or not each word satisfies the search conditions, such as the number of characters, the word familiarity and the representational plausibility; and extracts the word data satisfying the search conditions. Then, in the case of the search conditions, as shown in FIGS. 4 and 5, for example, 'RINGO ("apple" in Japanese)' is extracted from the word extractor 52.

The word acquirer 53 acquires a pair composed of a first word and a second word from the multiple word data extracted by the word extractor 52, and transmits said set of words to the word presenting means 2. On the occasion of the output, the first word is transmitted to the word presenting means 2 first, and then, after the preset period of time has passed, the second word is transmitted to the word presenting means 2. Further, any words, which have been acquired once and presented to the word presenting means 2, are designed not to be newly acquired. Further, the word acquirer 53 transmits a trigger pulse of the start time to present a word to the action index data calculator 56 and the brain activity data calculator 57.

The operation signal acceptor 54 accepts an operation signal from the operation unit 4 and transmits the signal to the action index data calculator 56.

The brain activity measurement data acceptor 55 accepts the brain activity measurement data from the brain activity measuring unit 3 and transmits the data to the brain activity data calculator 57.

The action index data calculator 56 receives a trigger pulse of the start time to present a word from the word acquirer 53; receives an operation signal from the operation signal acceptor 54; and calculates the reaction time up until recognizing the presented word by the subject H. In addition, it determines whether or not the subject correctly answers the presented word, and calculates the percentage of questions answered correctly, based upon the operation signal.

The brain activity data calculator 57 receives a trigger pulse of the start time to present a word from the word acquirer 53; additionally receives the brain activity measurement data from the brain activity measurement data acceptor 55; conducts signal processing of the data, such as averaging, filter processing or activity source estimation; calculates the brain activity time period indicating the time variation of the brain activity in the subject or the brain activity position data as indication of the position of brain activity in the subject; and transmits the data to the output unit 7.

Figure 6:
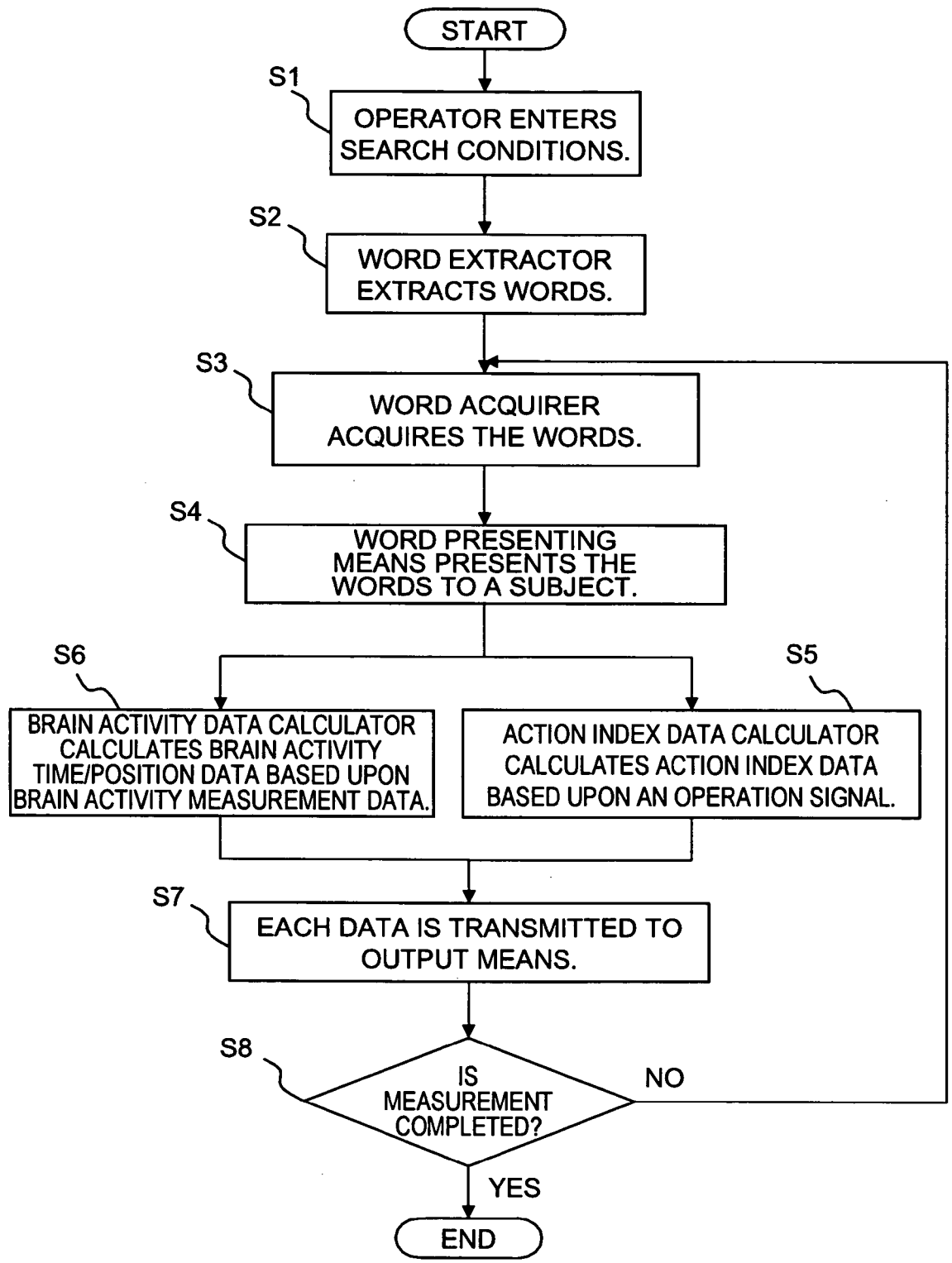
FIG. 6 is flowchart showing the language processing function measuring device in said embodiment.

Next, a language processing function measuring device 1 having this construction is described with reference to FIG. 6.

First, an operator enters search conditions using the input means 6 (Step S1). The search condition data acceptor 51 receives the search condition data indicating the search conditions, and transmits the search condition data to the word extractor 52. Then, the word extractor 52 extracts the word data based upon the search condition data (Step S2). The extracted word data is primarily stored, for example, in the memory 502 of the operating device 5.

After that, the word acquirer 53 acquires the word data per pair from the word data stored in the memory 502 and transmits the word data to the word presenting means 2 (Step S3), and the word presenting means 2 presents a first word (prime) to the subject H, and then presents a second word (target) next (Step S4).

The action index data calculator 56 calculates at least either the reaction time or the percentage of correct responses to the questions (task requirement) that were instructed to the subject prior to the experiment answered correctly based upon the trigger pulse and an operation signal synchronized by information (Step S5). Simultaneously, the brain activity data calculator 57 calculates at least either the brain activity time data or the brain activity position data, based upon the trigger pulse and the brain activity measurement data (Step S6). After that, these data are transmitted to the output means 7 (Step S7). When the measurement is completed (Step S8), the measurement is finished there, and if not, the word acquirer 53 newly acquires a pair of words and transmits said pair to the word presenting means 2, and the similar operation continues.

According to the language processing function measuring device 1 having this construction, words accurately controlled by the set conditions can be extracted, so the time and effort required for the word extraction can be reduced. In addition, an adverse effect on measurement data can be reduced, and the reliability of experimental results can be improved. Further, because a trial and error by manual procedures can be completed in a short time, the results can be fed back to the condition setting to obtain the necessary number of words. As described above, because the condition setting for the number of words to be extracted, for the number of characters and for the category level can be optimized under the conditions to obtain the necessary number of words, any adverse effect to affect the reaction, such as brain activity, can become as less as possible, and the reliability of experimental results can be improved.

In addition, regarding the category, it is possible to variously set conditions, for example, belonging to the same category, relevance to the one-upper level, not belonging to said category by contraries, or opposite from the viewpoint of the category, and regarding the word characteristics, such as a visual form, phonology or a semantics, it is possible to variously set conditions, as well.

Further, depending upon the manner of setting the conditions, a difference of the brain activities, using familiar or unfamiliar words, rare words or well-known words but having an unfamiliar representation and a learning effect according to repeatedly seeing a list of unfamiliar words can be measured. The present invention can test an understanding of a category and a semantics in the examination of aphasia patients, and the present invention can also preferably be used for an examination of the degree of development of speech and language or the degree of understanding for infants.

Furthermore, the present invention is not limited to the above embodiment.

For example, in the embodiment, it is designed such that the word data extracted by the word extractor is acquired by the word acquirer, and the data is presented by the word presenting means. However, it can be designed such that only words are extracted by the word extractor in advance and saved into, for example, a floppy disc, and reading the floppy disc by a computer at the time of measurement results in the acquirement of the words by the word acquirer and the presentation by the word presenting means.

Depending upon the designed use of this experiment, for example, it can be designed such that category and attribute of dialect, and category and attribute of the baby talk can be stored in the databases, respectively.

In addition, the present invention can be applied to a category experiment presenting three or more words one after another or an experiment to obtain a category decision by presenting a single word.

Further, the brain activity measuring means is not limited to MEG (magnetoencephalography), and it is needless to say, EEG (electroencephalography), functional magnetically resonance imaging (fMRI), PET (positron CT) or NIRS (near-infrared light spectroscopy imaging) can be used.

It is possible to variously modify the present invention without departing from the scope of the invention.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. In a language processing function measuring device, which is equipped with a word presenting unit to present words to a subject, a biological activity measuring unit to measure a biological activity of the subject and a calculation unit to calculate information measured by the biological activity measuring unit, the improvement comprising:
the calculation unit includes a word database where word data indicating words are presented to the subject, a category data of the words, and attribute data of the words are related and then stored, respectively, and, a word extractor to search the word database and to extract words belonging to or relating to a predetermined category, and satisfying a predetermined attribute, based upon predetermined search conditions that are entered by a user, and the word presenting unit presents a portion of or entire words indicated by the word data indicating words extracted by the word extractor.

2. The language processing function measuring device according to claim 1 wherein the word extractor additionally extracts word data indicating words with a predetermined number of characters.

3. The language processing function measuring device according to claim 1 wherein the category hierarchically indicates the classification of words and the attribute contains word familiarity, which is an index indicating the degree of word familiarity to a population representative of the subject showing how much the word is familiar, and representational plausibility, which is an index indicative of plausibility of word representation, such as Katakana, Hiragana or Kanji in Japanese.

4. The language processing function measuring device according to claim 1, wherein, the biological activity measuring unit is equipped with a brain activity measuring unit to measure the brain activity in the subject and the calculation unit calculates at least either brain activity time data indicating the time variation of the brain activity in the subject or brain activity position data indicating the position of brain activity in the subject based upon the brain activity measurement data from the brain activity measuring unit.

5. The language processing function measuring device according to claim 1, wherein, the biological activity measuring unit is equipped with an operation unit to be subjectively operated when the subject recognize the words; and
the operation unit is equipped with an action index data calculator to calculate action index data indicating at least a reaction time and a percentage of questions answered correctly by the subject based upon an operation signal from the operation unit.

6. The language processing function measuring device according to claim 1 wherein the word presenting unit presents at least a first word and a second word, which are established from word data extracted by the word extractor, at a predetermined time interval.

7. The language processing function measuring device according to claim 1 that is equipped with a search condition data acceptor for accepting the search condition data from an operator, and wherein the word extractor searches the word database and extracts word data indicating words belonging to or relating to the predetermined category, and, satisfying a desired word attribute, based upon the search condition data accepted by the search condition data acceptor.

8. The language processing function measuring device according to claim 7 wherein the word extractor extracts word data indicating words with the predetermined number of characters, based upon the search conditions set by the operator.

9. The language processing function measuring device according to claim 7 where the search conditions are composed of multiple logical formula for search conditions.

10. A language processing function measuring device, comprising:
a word presenting unit to present words to a subject;
a biological activity measuring unit to measure the biological activity of the subject; and
a calculation unit to calculate information measured by the biological activity measuring unit; and
the calculation unit is equipped with word databases where word data indicating words to be presented to the subject, category of the words and attribute data of the words are related and then stored, respectively, and a word extractor to search the word databases and to extract the word data belonging to or relating to a predetermined category, and, satisfying predetermined word attribute, based upon the search conditions; and the word presenting unit presents a portion of or entire words indicated in the word data extracted by the word extractor;

in addition, the biological activity measuring unit is equipped with a brain activity measuring unit to measure brain activity in the subject; and the calculation unit is equipped with a brain activity data calculator to calculate at least either brain activity time data indicating the time variation of the brain activity in the subject or brain activity position data indicating the position of the brain activity in the subject based upon the brain activity measurement data from the brain activity measuring unit.

11. The language processing function measuring device according to claim 10, wherein, the biological activity measuring unit is equipped with an operation unit to be subjectively operated when the subject recognizes the words, and the calculation unit is equipped with an action index data calculator to calculate action index data indicating at least either the reaction time or percentage of questions answered correctly by the subject, based upon an operation signal from the operation unit.

12. The language processing function measuring device according to claim 10 wherein the word presenting unit presents at least a first word and a second word established from the word data extracted by the word extractor at a predetermined time interval.

13. The language processing function measuring device according to claim 10 that is equipped with a search condition data acceptor for accepting the search conditions from an operator, and wherein the word extractor searches the word databases and extracts the word data indicating words belonging to or relating to a predetermined category, and, satisfying desired word attribute, based upon the search condition data accepted by the search condition data acceptor.

14. The language processing function measuring device according to claim 13 wherein the word extractor extracts word data indicating words with the predetermined number of characters, based upon the search conditions set by the operator.

15. The language processing function measuring device according to claim 13 wherein the search conditions are composed of multiple logical formula for search conditions.

\* \* \* \* \*